United States Patent [19]

Gram

[11] Patent Number: 4,905,502

[45] Date of Patent: Mar. 6, 1990

[54] PRESSURE VESSEL FATIGUE TEST SYSTEM

[75] Inventor: Martin M. Gram, St. Louis Park, Minn.

[73] Assignee: MTS Systems Corporation, Eden Prairie, Minn.

[21] Appl. No.: 332,448

[22] Filed: Mar. 31, 1989

Related U.S. Application Data

[63] Continuation of Ser. No. 153,959, Feb. 9, 1988, abandoned.

[51] Int. Cl.$^4$ ............................................. G01M 3/04
[52] U.S. Cl. ...................................... 73/49.4; 73/167; 73/49.6
[58] Field of Search ................. 73/808, 810, 813, 816, 73/837, 49.4, 49.6, 37, 4 R, 4 D, 167, 865.6, 49.5

[56] References Cited

U.S. PATENT DOCUMENTS

| | | | |
|---|---|---|---|
| 1,282,120 | 10/1918 | Patterson | 73/49.4 |
| 2,048,027 | 7/1936 | Preston | 73/49.4 |
| 2,326,345 | 8/1943 | Ernst et al. | 73/49.4 |
| 3,693,432 | 9/1972 | Stewart et al. | 73/167 |
| 3,842,665 | 10/1974 | Sober | 73/816 |
| 4,263,807 | 4/1981 | Brown et al. | 73/167 |
| 4,274,290 | 6/1981 | Gram | 73/837 |
| 4,290,343 | 9/1981 | Gram | 73/837 |

FOREIGN PATENT DOCUMENTS 0926571 5/1982 U.S.S.R. ................., ..................... 73/816

*Primary Examiner*—Robert R. Raevis
*Attorney, Agent, or Firm*—Kinney & Lange

[57] ABSTRACT

A pressure vessel fatigue test system has an adjustable mounting arrangement for a pressure vessel that can have open ends or closed ends, and which is to be subjected to a very high value, short duration pressure pulses, under controlled test conditions, to determine fatigue life of the vessel. In order to provide a pulse of high pressure that smiulates pulse pressures that may be present in the vessel, a cylinder having a bore filled with hydraulic oil is open to the interior of the vessel, and the vessel is also filled with hydraulic oil. A pressure generating piston is slidable in the bore or the cylinder and has a substantial mass that is attached to it. The mass is accelerated rapidly under control of an actuator in response to a control signal. When the piston first moves from a retracted position the oil in the cylinder bore is displaced into a low pressure accumulator. After the piston moves a sufficient distance so that the velocity of the mass has reached a desired level and there is substantial kinetic energy in the system, the plunger seals off a bore and the piston and mass decelerate rapidly and a pulse of pressure is applied to the test vessel across a short span of time.

6 Claims, 3 Drawing Sheets

PRESSURE VESSEL FATIGUE TEST SYSTEM

This is a continuation of application, Ser. No. 153,959, filed Feb. 9, 1988 (now abandoned).

BACKGROUND OF THE INVENTION

1. Field of the Invention.

The present invention relates to a fatigue test system for closed pressure vessels where a high pressure of extremely short duration is used for testing.

2. Description of the Prior Art.

In the prior art, pressure vessels have been tested with cyclic pressures, but it has been difficult to obtain high value pulse of pressure of short durations that will adequately simulate operating conditions for tubular pressure vessels such as a breach of a cannon or gun. The present device provides a way of imparting velocity to a mass coupled to a piston to provide a substantial amount of kinetic energy and utilizing that kinetic energy for generating a pressure pulse of sufficiently high pressure level in a short time.

SUMMARY OF THE INVENTION

The present invention relates to a pressurization test system for closed pressure vessels for fatigue testing such pressure vessels, wherein the pressure vessels are subjected in use to very high value pressure pulses of very short duration. An example of the type of pressure pulses would be operating pulses produced in a shell chamber of a mortar or military cannon or gun, where high pressures are generated in a pulse form when a shell is fired. Accurate analysis of the fatigue life of the breaches of such guns permit accurate determination of times of decommissioning or changing components of such guns.

The test system of the present invention comprises a support for a pressure vessel, and where necessary provides a base that closes off one end of an open pressure vessel. The upper opposite end of the pressure vessel (the vessel is usually oriented with its axis vertical) is coupled through a sealing plug to an energy imparting fatigue test cylinder and piston assembly. The cylinder has a relatively small piston bore that opens into the pressure vessel. The pressure vessel and the bore is with the piston retracted filled with a fluid having a high bulk modulus (hydraulic oil or water). The bore has a port in a center portion of this cylinder leading to a low pressure accumulator. The piston comprises an elongated rod that slides in the bore from a retracted position toward the port and thus toward the pressure vessel when it is to be used. The bore is filled with fluid from the low pressure accumulator when the piston is retracted to its initial position. The piston, comprising the elongated rod, is controlled by a hydraulic actuator or velocity generator that will hold the piston in its retracted position. A substantial mass comprising a number of individual weights are directly mounted onto the elongated rod comprising the piston.

When the hydraulic actuator that holds the piston rod retracted is triggered to release, it will be accelerated by hydraulic oil from a second accumulator. The hydraulic oil is ported through a rapid opening poppet valve into the actuator to in turn accelerate the piston and the mass along the bore of the fatigue test cylinder assembly. Because the second accumulator is at a high pressure, there is a substantial velocity attained. The hydraulic oil that is displaced by initial movement of the fatigue test piston will be ported to the low pressure accumulator connected to the cylinder with substantially no resistance. The fatigue test piston moves past the port of the low pressure accumulator at a desired velocity. The mass has then reached the desired velocity, and therefore carries a desired amount of kinetic energy. The end of the piston will seal on the bore surface after it passes the port so that all of the energy in the mass attached to the fatigue test piston will be imparted by the piston to the fluid enclosed within the bore of the fatigue test cylinder assembly and the pressure vessel and to expand those vessels. The high bulk modulus fluid (hydraulic oil or water) therefore changes the kinetic energy of the mass into potential energy causing a very high pressure pulse of a short duration (depending on the parameters selected) that will act against the walls of the pressure vessel for testing purposes.

The velocity of the mass can be controlled and varied to insure that the pressure pulse achieved is at the desired level. The duration of the pulse can be varied by changing the size of the mass.

The fatigue test system utilizes existing controls, but includes a unique arrangement for permitting the mass and piston to accelerate to a desired velocity without substantial restraint and yet cause the kinetic energy of the mass to suddenly be imparted to a closed hydraulic cylinder and pressure vessel for the desired fatigue test.

The mass will tend to rebound after it has stopped against the hydraulic oil in the pressure vessel. The rebound velocity will be at substantially the same velocity, but opposite sign as the initial velocity. The actuator can be programmed to close the poppet valve as the actuator reaches the top of the rebound stroke. This prevents a second impact and also has the effect of trapping oil in the accumulator, thereby saving energy. Various safety devices and make-up oil arrangements can be provided as desired.

The use of an adjustable crosshead for mounting the test pressure vessel permits adaption of the system for a wide variety of pressure vessels of different sizes, some of which have at least one closed end and others which have both ends open, and which are plugged for the test.

DETAILED DESCRIPTION OF THE PREFERRED EMBODIMENT

Figure 1:
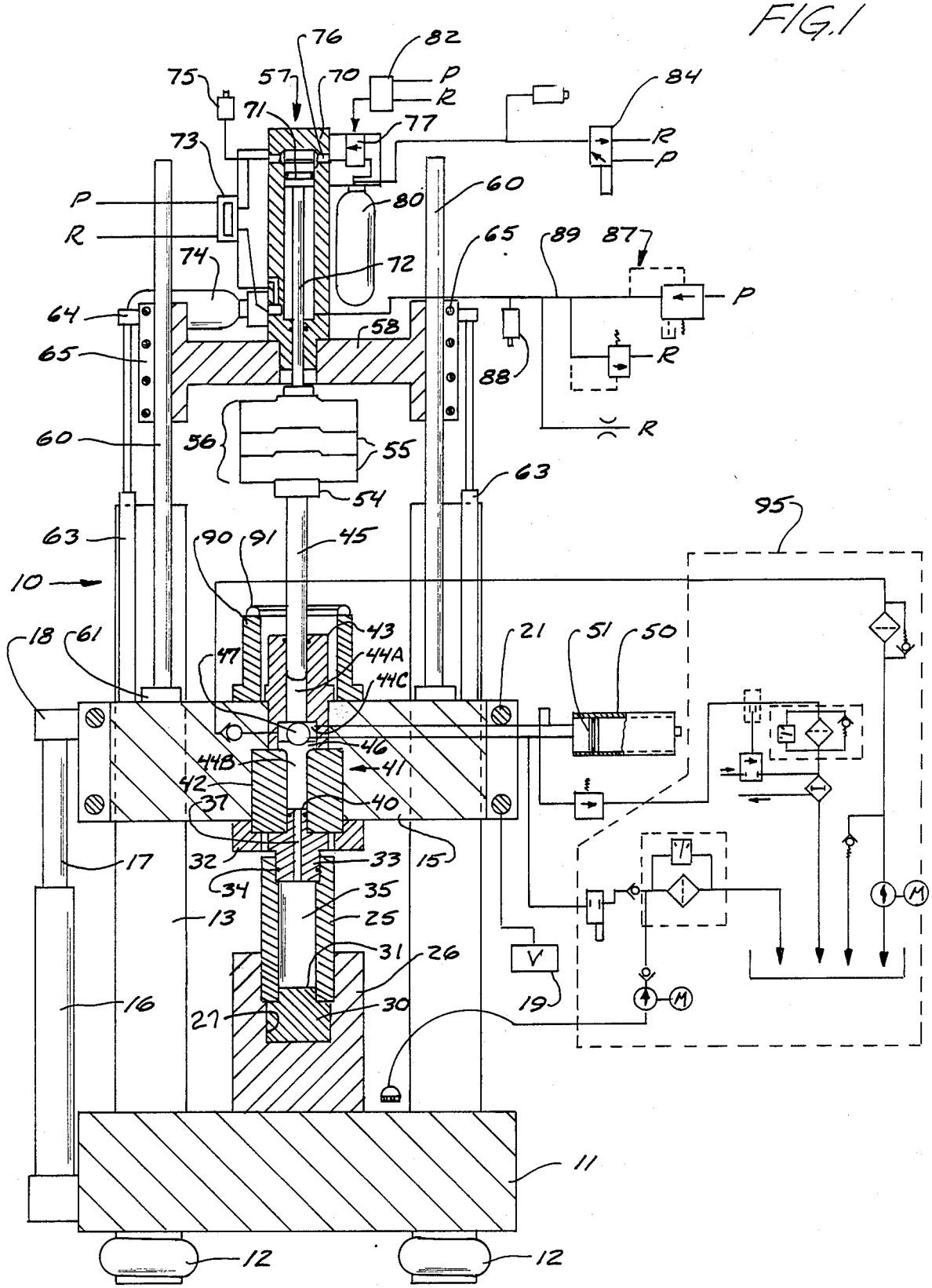
FIG. 1 is a schematic sectional view of a fatigue test system made according to the present invention showing schematic control arrangements therefor.
Figure 2:
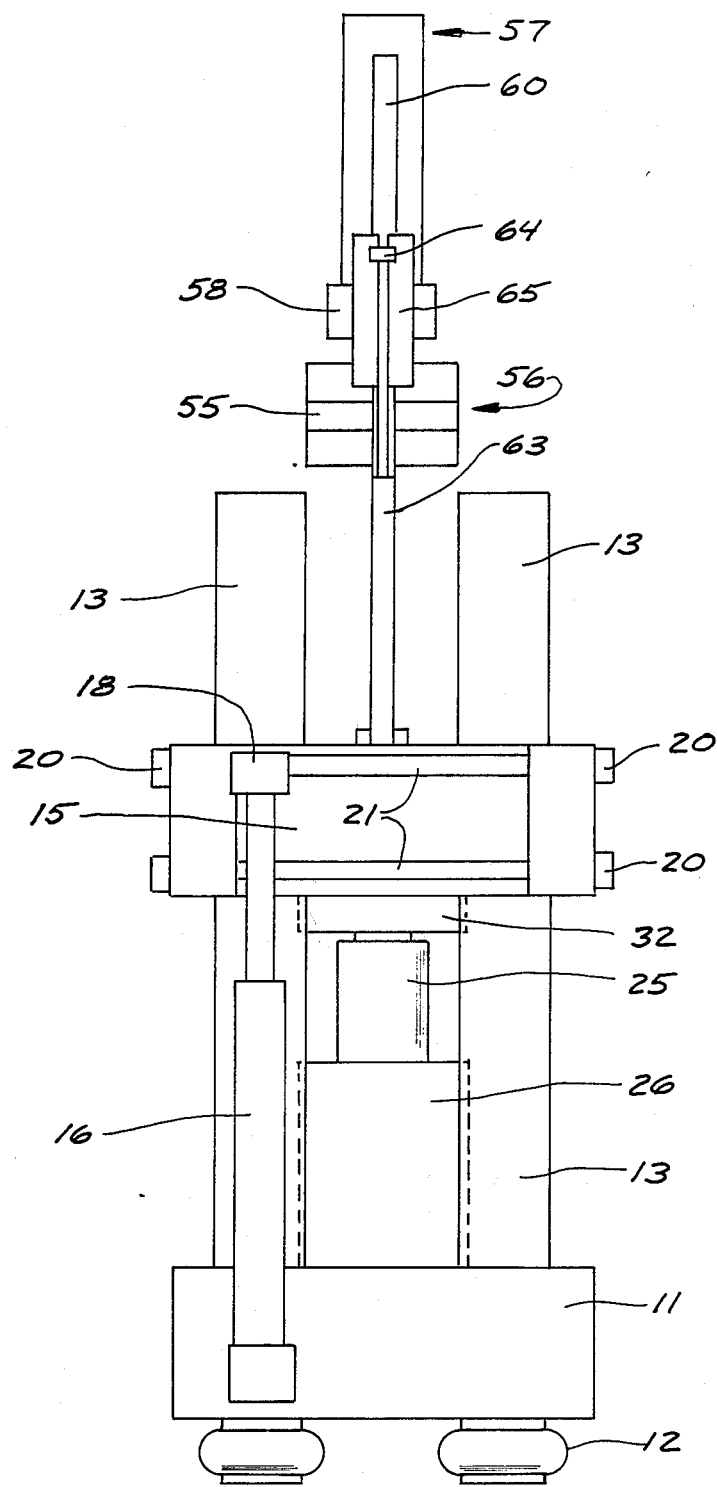
FIG. 2 is a side view of the test apparatus of FIG. 1.

As shown in FIG. 1, the fatigue test apparatus indicated generally at 10 includes a heavy base 11, mounted on suitable air filled isolation bags 12 in a conventional manner. The base 11 supports four columns 13 that comprise main columns for holding the test apparatus. The columns 13 extend vertically and have a crosshead or platen 15 suitably slidably mounted thereon. The platen 15 can be raised and lowered through the use of hydraulic actuators 16 at opposite ends of the cross head 15 extending between the base 11 and the crosshead, and which have a double acting rod 17 coupled as at 18 to the crosshead. Suitable clamps 20 that can be hydraulically operated clamp onto tie bolts 21 to clamp the crosshead in its desired axial location along the columns 13. A valve 19 can be provided for controlling the hydraulic clamps.

A test specimen indicated at 25 is shown schematically as a pressure vessel tube. This type of a vessel or tube can have any desired internal shape, but it has one end supported on a specimen support block 26 mounted onto the base 11 with an interior receptacle 27. The lower end of the receptacle 27 has a spacer block 30, which supports a suitable seal or cap member 31 that can be inserted into the lower end of the tubular pressure vessel or specimen 25 for sealing it.

Crosshead 15 supports a vessel cap 32 on its lower side, which has a neck 33 that fits within the pressure vessel 25, and which has a suitable seal 34 thereon which seals the interior chamber indicated at 35 in the pressure vessel or specimen 25. The cap 32 is suitably fixed to the lower side of the crosshead 15, and has an internal passageway 37 that opens to the interior chamber 35 of the pressure vessel or specimen. The passageway 37 also extends into a neck portion 40 of the cap that fits within a fatigue test cylinder assembly indicated generally at 41 that fits in a passageway extending through the cross head 15. The fatigue test cylinder assembly 41 has a first section 42 in which the neck 40 fits, and section 42 is mounted into a suitable opening in the crosshead 15, and the fatigue test cylinder assembly 41 further has a second fatigue test cylinder section 43 that mates with the section 42. The section 43 extends up to the upper side and through the crosshead 15, and the two sections each have internal bore portions 44A and 44B, respectively, that is of size to closely fit and seal with respect to an elongated fatigue test piston 45.

The cylinder bore portions 44A and 44B are connected to each other through an intermediate cylinder bore portion or chamber 44C which is of larger diameter than the piston 45, and as shown the cylinder chamber 44C has a tapered (rounded) transition indicated at 46 that merges with the lower cylinder section. The larger diameter cylinder chamber 44C is open to a port 47 formed in the fatigue test cylinder, that leads to a low pressure accumulator means indicated schematically at 50. The schematic showing represents a piston type accumulator that will hold a substantial volume of oil at a relatively low pressure. More than one accumulator 50 can be connected to port 47. A high bulk modulus fluid (hydraulic oil, for example) is kept on the side of the piston 51 closest to the port 47, and a suitable gas under a desired pressure is on the opposite side of the piston within the accumulator 50. This hydraulic fluid fills the passageway leading from the accumulator to the fatigue test cylinder and also fills the interior of the bore portions 44A and 44B that are open to the port 47, with the fatigue test piston retracted.

The upper end of the elongated (rod-like) fatigue test piston 45 has a collar 54 fixed thereto that is made to support a number of individual weights 55 that together comprise a mass 56 that is movable axially with the piston 45. The fatigue test piston 45 is held in a raised position as shown in FIG. 1 and accelerated downwardly through the use of a velocity control actuator 57 that in turn is mounted on and which extends above a crosshead 58. The crosshead 58 is slidably guided on a plurality of columns 60 that in turn are fixed as at 61 to the upper side of the main crosshead 15. The position of the upper crosshead 58 on the columns 60 is controlled through actuators 63 that are mounted on the top side of the crosshead 15 and have rod ends connected as at 64 to the crosshead 58. Suitable column clamps indicated generally at 65 are used for clamping the crosshead 58 to the columns 60. These can be conventional hydraulic clamps used on crossheads of specimen test machines.

The velocity control actuator 57 has an outer housing 70, and an internal piston 71 that is connected to a rod 72. The rod 72 is mounted onto the fatigue test piston 45 and the mass 56. The velocity control actuator piston 71 is raised to its raised level by providing hydraulic oil through a servovalve 73. The mass 56 and the fatigue test piston 45 are held in the raised position until released. An accumulator 74 is used for receiving the fluid from the lower side of the piston 71 when the piston 71 drops, as will be explained. A suitable pressure transducer indicated at 75 is utilized for sensing pressure above the piston 57.

A passageway 76 at the upper end of the housing 70 leads to a rapid opening and position controllable poppet valve 77. The poppet valve 77 in turn controls flow from one or more large volume accumulators 80 that are mounted onto the poppet valve 77. A poppet valve such as that shown in U.S. Pat. No. 4,290,343, issued Sept. 22, 1981, includes a mechanical speed control stop that is satisfactory. In the present device, the mechanical speed control stop is replaced with a servovalve controlled stop.

The rapid opening poppet valve 77 is released, as taught in U.S. Pat. No. 4,290,343, or as shown here is controlled by means of servovalve 82, which when receiving a signal will cause the poppet valve 77 to open, after which the poppet valve 77 opens very rapidly to its controlled or stop position to discharge the fluid in the accumulator 80 into the interior of the velocity control actuator housing 70, acting on the piston 71 to force it downwardly so it reaches a desired velocity. The fluid on the rod side of piston 71 flows into accumulator 74. The servovalve 73 remains closed. The servovalve 82, as stated, controls the open position of the poppet valve 77 in response to a command signal and feedback from a stroke transducer which measures the position of the poppet valve directly in a known position control servoloop.

A valve arrangement indicated generally at 87 can be utilized for insuring that the oil on the bottom side of the piston 71 will be at the proper pressure so that the accumulator 74 is able to receive it when the piston moves down. A pressure transducer 88 can be used for sensing the pressure in line 89 in order to check that the pressure is at the correct level before opening the poppet valve 77.

Figure 3:
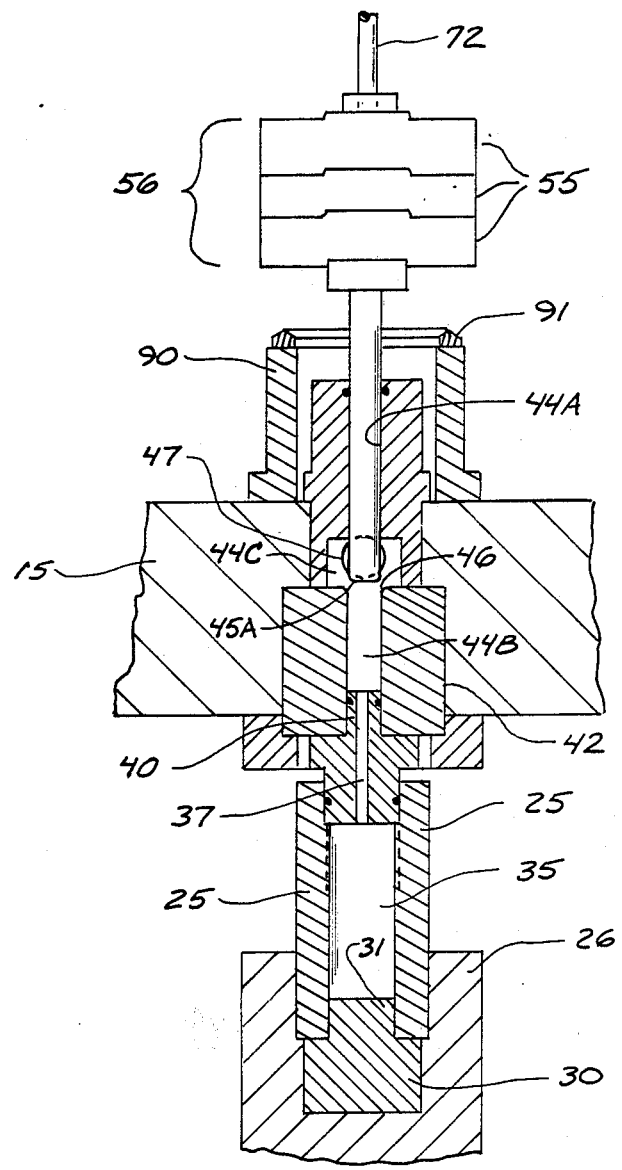
FIG. 3 is a fragmentary enlarged sectional view of the fatigue test cylinder and piston arrangement showing the piston in a position where it is closing off the fatigue test cylinder bore to impart a pressure pulse to a vessel being tested.

When the test pressure vessel or specimen 25 is in place, and the volumes of interior chamber 35, the passageway 37, and the bore portions 44A and 44B are filled with fluid (hydraulic oil), and the accumulator 50 is filled as well through a make-up oil valve network 95, the fatigue test system is ready to be used. A signal is provided to a servovalve 82 for releasing the poppet valve 77 to permit the fluid under pressure from the accumulator (or accumulators) 80 to flow into the velocity control actuator 57 to force the piston 71 downwardly and permit the mass 56 to be urged downwardly as well as having gravity act on the mass 56 to increase its velocity. At this same time, the fatigue test piston 45 is forcing oil out of the bore portion 44A of the fatigue test cylinder, which then flows freely through the port 47 leading from the fatigue test cylinder chamber 44C into the accumulator 50. The accumulator 50 is a low pressure, high volume accumulator and as stated, there may be more than one such accumulator 50 open to port 47. The flow of oil or fluid into accumulator 50 does not substantially restrict the free fall of the mass 56 or the acceleration of the mass and the piston 45 toward the fatigue test cylinder bore portion 44B. As can be seen in FIG. 3, when the end portion 45A of the fatigue test piston is moving into the tapered or rounded surfaces 46 of the fatigue test cylinder bore, the fluid that is being displaced to port 47 will be restricted as the flow area is reduced. As the flow is restricted, the pressure in the volume of oil in cylinder bore portion 44B starts to increase. When the full size diameter of the fatigue test piston 45 reaches the level substantially at the interface line between the cylinder portion 42 and the cylinder section 43 (see FIG. 3), it will close the lower fatigue test cylinder bore portion 44B and oil in the test vessel or specimen chamber 35 and in the passageway 37 and fatigue test cylinder bore portion 44B will be trapped and will receive the energy developed in the fatigue test piston 45 and mass 56. Suitable seals that can be provided for the fatigue test piston 45 or a metal to sliding metal seal may be adequate, depending on the application. In other words, there may be some low friction seals on the interior of the fatigue test cylinder bore portion 44B that will seal on the piston 45 as it passes into bore portion 44B.

The piston 45 closes off substantially all escape routes for the trapped oil or hydraulic fluid, and the mass energy will be converted to potential energy in the fluid within the chamber 35 of the test vessel or specimen 25. This will cause the mass to decelerate rapidly causing a pulse of pressure of high magnitude and short duration to be present in the fatigue test cylinder bore portion 44B, the passageway 37, and the interior chamber 35 of the test vessel or specimen 25. The sudden deceleration causes a high impulse of pressure on the interior of the test vessel or specimen for test purposes.

The mass 56 will tend to rebound, once the trapped oil has stopped the downward velocity of the mass. The upward velocity of the mass will be slightly less than the downward velocity before the pressure pulse. The reduction is due to friction losses in the system.

As the mass moves upward, flow is reversed to each accumulator, and the mass therefore is decelerated. If the poppet valve 77 was to be left open, the mass would stop and the process would be repeated at a progressively lower velocity and pressure pulse as energy in the system is converted to friction. To prevent the multiple pressure pulses, the poppet valve 77 is closed as the actuator reaches the top of its travel. This has a secondary effect of trapping a substantial amount of fluid in the accumulator 80, which saves energy.

When the poppet valve 77 has closed and the actuator has stopped, the mass 56 can be lifted by actuating the servovalve 73 to move the velocity control actuator piston 71 upwardly and the accumulator 80 can be recharged through a valve solenoid 84. Repeated pressure pulses controlled as described for one cycle are applied to the tubular test vessel or specimen 25 for completion of a fatigue test.

A collar 90 is provided around the upper portion of the fatigue test cylinder 43, and it has an energy absorbing pad 91 thereon which will serve to arrest motion of the mass, to protect the system if the specimen fails for example. In other words, if the test vessel or specimen 25 should break and the mass 56 fall freely, it would strike the energy absorbing pad or ring on the collar 90.

The volume of cylinder chamber or bore portion 44C can be filled and controlled through a suitable pressure control valve arrangement 95 of conventional design, for recharging as desired, and for insuring that the volumes of fatigue test cylinder bore portion 44B, passageway 37, and the interior chamber 35 of the test vessel or specimen 25 are filled. The passageway 37 is sufficiently large so that the interior chamber 35 will fill with oil under gravity. The piston 45 would be lowered during the initial fill cycle to insure removal of all the air.

The retraction of the mass 56 can be accomplished relatively rapidly, so the fatigue tests can be repeated. Pressures in the range of 100,000 psi can be generated, with pressure pulses ranging for example down to about 5 milliseconds, so that rapid pulses of high pressure are possible with the fatigue test system.

The pulse duration can be controlled by varying the mass, and the amplitude is determined by the velocity of the mass at the time the fatigue test piston 45 closes off the lower test cylinder section. A large mass at a lower velocity, which provides a desired level of energy, will provide for a long duration pulse, while a lower mass with more velocity, which provides the same energy, will provide a shorter pulse.

The fatigue test system shown in FIG. 1 comprises a velocity generating section including the actuator 57, and the mass 56; a velocity to pressure conversion section comprising the fatigue test cylinder 43, and the interior cylinder bore portions 44A and 44B and chamber 44C, together with the fatigue test piston 45; and a reaction section where the test specimen 25 is mounted. The velocity generator section further includes the controls, including the poppet valve which is made to allow high flow, for example, 30,000 liters per minute.

The adjustable crosshead 58 can be moved to permit mounting different size masses, and for adjusting the level of the mass and piston to the required position. The mass can be a series of disc-like weights 55, or can be other types of weights as desired. The discs can be held in place with suitable fasteners so there is no danger of the discs becoming unattached.

The velocity generator actuator 57, and the fatigue test piston 45 are concentric or coaxially, so there is in-line movement during acceleration or velocity build-up.

Although the present invention has been described with reference to preferred embodiments, workers skilled in the art will recognize that changes may be made in form and detail without departing from the spirit and scope of the invention.

What is claimed is:

1. A fatigue test apparatus for testing a pressure vessel having an interior chamber comprising:
   a frame;
   means for supporting a pressure vessel to be tested on the frame;
   a fatigue test cylinder on the frame open to a pressure vessel on the means for supporting;
   a piston member mounted in said fatigue test cylinder and movable in said fatigue test cylinder from a first position toward the means for supporting;
   means for imparting velocity to said piston member in said fatigue test cylinder;
   means for permitting fluid to bleed from the fatigue test cylinder as the piston member moves therein during initial movement of the piston member from its first position toward the means for supporting, and for closing off flow from said fatigue test cylinder to generate pressures therein as a function of the energy of the piston member when the piston member has reached a selected velocity related energy level; and means for providing a fluid with a high bulk modulus to the interior of the fatigue test cylinder and the interior of a pressure vessel mounted on the means for supporting prior to initial movement of the piston member from its first position.

2. The fatigue test apparatus of claim 1 wherein said means for permitting fluid to bleed from the fatigue test cylinder comprises means defining a port in the fatigue test cylinder spaced from the piston member in its first position, and a low pressure accumulator connected to said port, said accumulator comprising part of the means for providing fluid.

3. The fatigue test apparatus of claim 1 wherein the means for closing off flow comprises a fatigue cylinder section having a bore to closely fit the periphery of the piston member.

4. The fatigue test apparatus of claim 1 wherein the means for imparting velocity to the piston member comprises an actuator driving the piston member toward the means for supporting.

5. The fatigue test apparatus of claim 4 and separate means forming a mass connected to the piston member to create a major portion of the velocity related energy level of the piston member.

6. The apparatus as specified in claim 1 wherein the frame has a crosshead and a base, a support on the base for sealingly receiving a first end of a pressure vessel, and a sealing plug on the cross head for sealingly engaging a second end of a pressure vessel, said sealing plug having a passageway therein opening to one end of the fatigue test cylinder and open to a pressure vessel engaged by the sealing plug and mounted on said base, said frame reacting the force developed by the pressure acting on the sealed ends of the pressure vessel.

* * * * *